ROSE PLANT
Filed Sept. 23, 1969 2 Sheets-Sheet 1
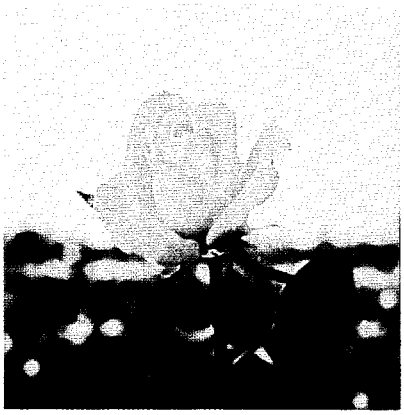

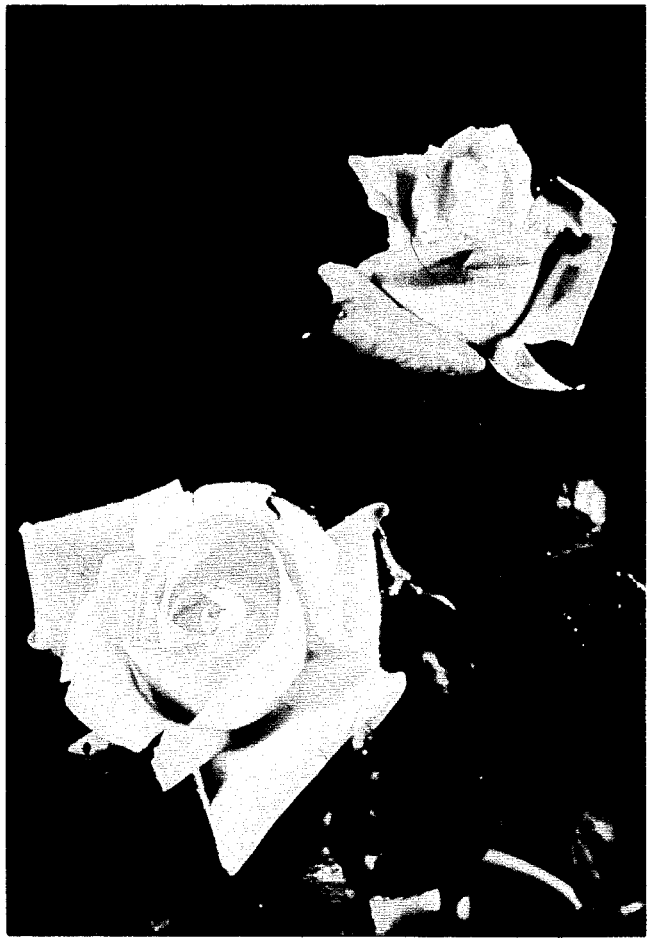

United States Patent Office

Plant Pat. 3,139
Patented Apr. 25, 1972

3,139
ROSE PLANT

Michel Kriloff, Antibes, France, assignor to Paul Pekmez, Strasbourg-Cronenbourg, France Filed Sept. 23, 1969, Ser. No. 860,441
Claims priority, application France, Sept. 25, 1968, 167,464
Int. Cl. A01h 5/00
U.S. Cl. Plt.—16 1 Claim The present invention relates to a new and distinct variety of rose plant of the hybrid tea class, having double flowers, being reddish salmon in color and having other characteristics which correspond to the needs of the horticultural industry for all uses related to the ornamentation of public and private gardens. The name of my new variety is Wizo.

In previous rose plants of this class, various undesirable characteristics have appeared, particularly weak vegetation, insufficient resistance to cryptogamic diseases, and insufficient inflorescence. In accordance with the present invention, these undesirable characteristics have been eliminated.

The instant variety has been asexually reproduced and its characteristics are stable.

After eliminating all the deficient or irregular as well as the subjects with characteristics outside the scope of research, the breeder proceeded to the grafting of the remaining subjects in order to pursue the research solely on rose plants and strictly in conformity with rose plants produced and commercialized by professional rose growers. Thereafter, a selection was made of the industrial plants so grown, leading to the elimination of all the grafted rose plants but that one which was the nearest combination of the desired characteristics.

The new rose plant produces double flowers with a generally orange color, with a shade darker on the inside petals than on the outside. It blooms abundantly from May to frost, and the reflorescence is excellent. It also has an excellent resistance to cryptogamic attacks.

The accompanying drawing shows a typical specimen of my new variety depicted in color.

The characteristics and properties of this variety obtained as above indicated are propagable by asexual ways, and in particular by grafting of budding eyes. The variety will be known under the following denomination: KRIwi 629. The botanic characteristics are as follows:

DESCRIPTION (Color references: Universal code of Mr. Seguy; Color chart of the Royal Horticultural Society (where indicated).

Class: Hybrid tea.

Plant:

*Height.*—39 to 40 inches.

*Growth.*—Erect.

Branches: Straight.

*Strength.*—Strong.

*Color.*—Reddish at the beginning, greenish on a mature wood.

*Thorns:*—Quantity—numerous, mixed with small prickles. Form—Hooked. Size—Average. Length—Average. Disposition—Grouped. Color—Young Branches—Purple Green 23I; Mature Wood—Green 357.

Foliage: Abundant.

*Texture.*—Smooth, tough.

*Color.*—At the beginning of vegetation—reddish.

*Petiole.*—Small hooked prickles occasionally appear.

*Leaflets.*—Number generally 5. Color—(at the blooming stage) inside—dark green 372. Outside—purple green 374. Form—from the base to terminal leaflets: lanceolated, slightly dentated.

*Inflorescense: Number of flowers by stem.*—Stem generally bears a single blossom.

*Peduncles.*—Rigid, smooth, covered with microscopic prickles. Length:—Average, 4 inches.

*Sepals.*—Long. Inside—slight tomentum, whitish. Outside—Smooth, light green with brown spots. Edge—Appendaged.

*Buds.*—Slender, and pointed at first, globular at calyx break. Volume: average.

Flower:

*Petalage.*—Double.

*Form.*—High centered, globular.

*Color.*—(Color chart of the Royal Horticultural Society). Inside of petals, Orange Group, B29; outside of petals, Orange Group, C 29. (In newly gathered flowers, color of inside petals, Red Group, between A 32 and B 33; outside of petals, Red Group, B 39); long lasting.

*Fragrance.*—None.

*Size.*—An average of 5"-6" in diameter when blossom is fully open.

*Petals.*—Texture—Very firm. Number—40. Behavior—do not drop by themselves. Persistence—Good.

*Stamens.* Number between 40 and 50. Anthers—Yellow 245. Threads: rose 255.

*Pistils.*—Number—between 20 and 30.
Stigma—yellow 24I.
Styles—rose 24I.

*Receptacles.*—Form—Gloubular. Aspect—Small.

Hips.—Light orange red, slightly marbled with green and maroon, spherical shaped.

Behavior:

*Persistence of inflorescence.*—Good

*Reflorescence.*—Good

*Vegetation.*—Very healthy

*Resistance to diseases and weather.*—Good.

I claim:

1. A new and distinct variety of rose plant of the hybrid tea class characterized by its long lasting, generally colored blossom, its ability to repeat bloom, good foliage and good disease resistance.

No references cited.

ROBERT E. BAGWILL, Primary Examiner

UNITED STATES PATENT OFFICE

CERTIFICATE OF CORRECTION

Patent No. Plant Patent 3139 Dated April 25, 1972

Inventor(s) MICHEL KRILOFF

It is certified that error appears in the above-identified patent and that said Letters Patent are hereby corrected as shown below:

In column 2, line 44, change "Gloubular" to --Globular--.

Delete the sheet of drawing identified as "2 Sheets-Sheet 1" and delete the description on the second sheet of drawings which now appears "2 Sheets - Sheet 2".

Column 2, line 54, after "generally" insert -- orange --.

Signed and sealed this 5th day of December 1972.

(SEAL)
Attest:

EDWARD M.FLETCHER,JR.
Attesting Officer

ROBERT GOTTSCHALK
Commissioner of Patents